United States Patent
Filippi et al.

(10) Patent No.: US 10,040,738 B2
(45) Date of Patent: *Aug. 7, 2018

(54) PROCESS AND PLANT FOR DISTILLATION OF METHANOL WITH HEAT RECUPERATION

(71) Applicant: Casale SA, Lugano-Besso (CH)

(72) Inventors: Ermanno Filippi, Castagnola (CH); Raffaele Ostuni, Milan (IT)

(73) Assignee: Casale SA, Lugano (CH)

( * ) Notice: Subject to any disclaimer, the term of this patent is extended or adjusted under 35 U.S.C. 154(b) by 726 days.

This patent is subject to a terminal disclaimer.

(21) Appl. No.: 14/374,173

(22) PCT Filed: Nov. 12, 2012

(86) PCT No.: PCT/EP2012/072353
§ 371 (c)(1),
(2) Date: Jul. 23, 2014

(87) PCT Pub. No.: WO2013/110368
PCT Pub. Date: Aug. 1, 2013

(65) Prior Publication Data
US 2015/0008116 A1    Jan. 8, 2015

(30) Foreign Application Priority Data

Jan. 23, 2012 (EP) .................... 12152185

(51) Int. Cl.
*B01D 3/14* (2006.01)
*C07C 29/80* (2006.01)
(Continued)

(52) U.S. Cl.
CPC .............. *C07C 29/80* (2013.01); *B01D 3/002* (2013.01); *B01D 3/007* (2013.01); *B01D 3/143* (2013.01); *C07C 31/04* (2013.01); *Y02P 70/34* (2015.11)

(58) Field of Classification Search
CPC ........ B01D 3/007; B01D 3/143; B01D 3/146; C07C 29/80; C07C 31/04
See application file for complete search history.

(56) References Cited

U.S. PATENT DOCUMENTS 2,148,712 A * 2/1939 Reich ..................... B01D 3/001
                                                   159/17.1
3,259,553 A * 7/1966 Halbritter ................ B01D 1/26
                                                   159/17.2
(Continued)

FOREIGN PATENT DOCUMENTS

EP        0210888 A1    2/1987

OTHER PUBLICATIONS

International Search Report issued in connection with PCT/EP2012/072353.
(Continued)

*Primary Examiner* — Jonathan Miller
(74) *Attorney, Agent, or Firm* — Akerman LLP

(57) ABSTRACT

Process and plant for refining crude methanol, comprising at least three distillation stages operating in cascade at decreasing pressures, wherein a first stage (200) operates at a maximum distillation pressure (p2), a second stage (300) operates at a medium distillation pressure (p3), and a final distillation stage (400) operates at a minimum distillation pressure (p4), wherein the first stage and the distillation stage each produce a respective gaseous stream (204, 304) of distilled methanol, and a respective solution containing methanol that is fed to the next distillation stage, and wherein at least one first gaseous stream of distilled methanol (204), produced in the first distillation stage, and a second gaseous stream of distilled methanol (304), produced
(Continued)

in the second distillation stage, are used as heat sources to heat the second distillation stage and the final distillation stage, respectively.

14 Claims, 2 Drawing Sheets

(51) Int. Cl.
  *C07C 31/04* (2006.01)
  *B01D 3/00* (2006.01)

(56) References Cited

U.S. PATENT DOCUMENTS

| | | | |
|---|---|---|---|
| 3,960,672 A | | 6/1976 | Ester et al. |
| 3,990,952 A | | 11/1976 | Katzen et al. |
| 4,210,495 A | * | 7/1980 | Pinto ............ B01D 3/146 203/18 |
| 4,592,806 A | | 6/1986 | Ilgner et al. |
| 5,294,304 A | * | 3/1994 | Kano ............ C07C 29/84 203/19 |

OTHER PUBLICATIONS

International Preliminary Report on Patentability issued in connection with PCT/EP2012/072353.

* cited by examiner

US 10,040,738 B2

PROCESS AND PLANT FOR DISTILLATION OF METHANOL WITH HEAT RECUPERATION

This application is a national phase of PCT/EP2012/072353, filed Nov. 12, 2012, and claims priority to EP 12152185.0, filed Jan. 23, 2012, the entire contents of both of which are hereby incorporated by reference.

FIELD OF APPLICATION

The present invention refers to a process and plant for distillation of methanol.

PRIOR ART

It is known that the product of plants for synthesising methanol, commonly defined as crude methanol, is an aqueous solution of methanol containing by-products of the synthesis reaction including ethanol, ketones, higher alcohols, and some dissolved gases including mainly H2, CO, CO2, N2, CH4.

The crude methanol is distilled to meet the purity specification required on the market. For example, the specification grade AA requires a minimum methanol concentration of 99.85% by weight, and requires that the ethanol does not exceed 10 ppm by weight.

Known distillation processes are based substantially on one or more refining columns. Generally, a refining column is able to separate a light product (for example gas) at the top, and a heavier product (e.g. aqueous solution) at the bottom or tail.

A first process and relative plant, widely used, comprises two columns that operate at atmospheric pressure or close to atmospheric pressure. More specifically, said process uses a preliminary treatment column known as topping column or pre-run column and a second distillation column. The first column substantially has the purpose of separating the more volatile components contained in the crude methanol; said column receives the crude methanol and separates the lighter components (light ends) at the top and an aqueous solution at the bottom; the second column carries out the actual distillation, obtaining: refined methanol at the top; a prevalently aqueous stream at the bottom ("bottom water"); a lateral stream known as "fusel oil" mainly containing water, residual methanol (ca. 1% of the total) and most of the by-products of the synthesis reaction. Said fusel oil has a certain heat value and is commonly used as a fuel.

Each column comprises a respective bottom reboiler that heats the bottom of the column and maintains the distillation process. The heat is provided by low-pressure steam, or by a process gas—when available—of a suitable thermal level. Moreover, each column requires a top reflux, i.e. part of the distilled methanol is condensed and re-introduced in the top of the column. For this purpose, each column is equipped with a respective top condenser that is normally water or air.

Said configuration with two columns is simple in terms of the plant, but it has the major drawback of consuming a substantial amount of energy both due to the heat supplied to the bottom reboilers, and due to the consumption of cooling water and/or electricity of the top condensers. Moreover, the columns have a relatively large diameter in relation to the production capacity and the plant cost is consequently high.

More specifically, the order of magnitude of the heat consumption of the two bottom reboilers is about 0.8 Gcal per ton of refined methanol. Since the energy consumption necessary to produce a ton of crude methanol is 6-8 Gcal, the order of magnitude of the energy consumption of the distillation is 10% of the total consumption of the plant. The heat disposed of in the condensers is comparable with the heat exchanged in the reboilers. In the theoretical case, for example, of removing said heat exclusively with cooling water, the flow rate circulating is noticeable, i.e. about 80 m3 per ton of methanol, and consequently there are high costs for pumping, etc.

There are known distillation plants and processes that attempt to at least partially reduce these drawbacks. U.S. Pat. No. 4,210,495 describes a process with three refining columns, i.e.: a preliminary treatment or topping column and two distillation columns, a column operating at a medium pressure of about 7-8 bar and a final distillation or bottoming column, respectively. The topping and final distillation columns operate substantially at atmospheric pressure or slightly higher pressure (e.g. 1.5 bar). Such a configuration makes it possible to condense the top vapours of the medium pressure column in the bottom reboiler of the final column at atmospheric pressure, recovering heat. However, both the topping column and the intermediate column must be heated and consequently the specific consumption, whilst being lower with respect to the plant with just two columns, is still high.

U.S. Pat. No. 4,592,806 describes an improvement of said process with three columns in which a fourth column treats two lateral streams of fusel oil coming from the two refining columns. Such a solution makes it possible to recover at least part of the methanol contained in the fusel oil that as stated above is about 1-1.5% of the total contained in the crude methanol and therefore is not negligible; however, such an improvement slightly increases the productivity but it does not substantially reduce the consumption. In particular the new column also comprises a bottom reboiler and a top condenser that respectively consume heat and cooling water or electricity.

The configurations described above are still widely used. Basically, the processes of the prior art still suffer from a substantial energy consumption of the order of 0.6-0.8 GCal per ton of methanol. There is a continuous incentive to reduce said consumption, as well as to reduce the heat to be disposed of in the top condensers of distillation columns. Another problem is represented by the size of the equipments (columns) which is proportional to the plant cost.

SUMMARY OF THE INVENTION

The invention has the purpose of reducing the consumption of energy, cooling water and/or electricity in a distillation process of crude methanol.

Such a purpose is accomplished with a process for refining a stream of crude methanol, comprising:
- at least three distillation stages operating in cascade at respective decreasing pressures, comprising at least one first distillation stage at a maximum distillation pressure, a second distillation stage at a medium distillation pressure, and a final distillation stage at a minimum distillation pressure,
- where said first and second distillation stage each produce at least one respective gaseous stream of distilled methanol and a respective solution containing methanol fed to the next distillation stage, and said final stage produces at least one gaseous stream of distilled methanol and a solution essentially made up of water;
- where at least one first gaseous stream of distilled methanol, produced in the first distillation stage, and a second gaseous stream of distilled methanol, produced in the second distillation stage, are used as heat sources for heating at least said second distillation stage and said final distillation stage, respectively.

The invention provides at least three distillation pressure levels, and in particular a first distillation stage at high pressure possibly preceded by a topping treatment for the separation of volatiles from the crude methanol. Preferably, said first distillation stage operates at a nominal pressure between 10 and 35 bar, and preferably at least 20 bar, according to the specific implementation.

It should be noted that in the prior art the maximum distillation pressure does not exceed the value of about 8 bar. The invention comprises a distillation stage operating at a relatively high pressure (for example 20 or 30 bar) and that requires a heat source with a high energy level, for example steam condensing at a pressure of 10 bar or higher. The applicant has found that a high pressure distillation stage increases the possibilities of heat recovery inside the distillation process itself, thanks to the availability of a gaseous stream of distilled methanol at a high temperature and pressure. It has been found that the improved heat recovery over-compensates for the need of a heat input at a higher energy level.

The term cascade means that a liquid solution containing methanol, obtained in a distillation stage, is further distilled in a subsequent stage. A generic intermediate distillation stage produces at least one stream of distilled methanol in gaseous state, and a solution of methanol intended for further distillation in the subsequent stage.

The last distillation stage is typically a so-called bottoming stage. The last stage typically produces distilled methanol in gaseous state, a solution mainly made up of water, and a side stream represented by the so-called fusel oil. Side streams of fusel oil can be extracted, if suitable, also from the intermediate distillation stages.

In some embodiments, the invention can also include more than three distillation stages, even if three stages are preferably adopted.

The term gaseous stream of distilled methanol means the stream resulting from a distillation process, for example taken from the top of a column. Such a stream is mainly made up of methanol, with low impurity content according to the required specification (e.g. grade AA).

Preferably, the pressures are determined so that said gaseous streams of distilled methanol can supply the full heat for a respective distillation stage that is located downstream in the cascade. For example, the stream of distilled methanol produced in the first stage supplies the full heat of the second stage, and so on.

Preferably, said gaseous streams of distilled methanol are at least partially condensed during the heat exchange, obtaining respective streams of distilled methanol in liquid state. For example, each gaseous stream of distilled methanol supplies the heat of a subsequent distillation stage by means of indirect heat exchange with a respective liquid solution containing methanol to be distilled. More preferably, the gaseous stream of distilled methanol condenses while the liquid solution evaporates. The condensation and evaporation, respectively, are at least partial and preferably they are total.

The liquid solution for example is taken from the bottom of a distillation column and the heated solution (partially or completely evaporated) is again fed to the bottom of the column, so as to heat the column.

In this way a joint evaporation and condensation step, is realized respectively of methanol solution (at a distillation pressure level) and distilled methanol (at a higher pressure level).

Said joint evaporation and condensation step can be carried out in a heat exchanger, for example tube bundle or plate exchanger, wherein the distilled methanol condenses in the hot side, and the solution evaporates in the cold side. The exchanger operates both as a bottom reboiler of a distillation column, and as a top evaporator of a higher-pressure column. Such a provision, according to one of the aspects of the invention, has the further advantage of eliminating the need for at least some of the top condensers, as will be made clearer hereafter with the help of examples.

The process can provide a preliminary topping treatment to remove the more volatile components. Said topping step is normally carried out at a pressure close to atmospheric pressure, typically 1-1.5 bar.

Another aspect of the invention consists of increasing the minimum distillation pressure (or bottoming pressure), contrary to the prior art where there is a tendency to maintain a bottoming pressure as low as possible and typically equal to the topping pressure. By raising the bottoming pressure, indeed, there is a further advantage in terms of energy, since the stream of distilled methanol produced in the last distillation stage has a sufficient temperature to be a heat source for the preliminary topping step.

For example, in some embodiments the topping pressure is roughly equal to atmospheric pressure, and the minimum distillation pressure is at least 2 bar and preferably about 5 bar.

In other words, the applicant has found that contrary to the prior art—which incentives to distillation at the lowest possible bottoming pressure, and typically equal to the topping pressure—the adoption of a substantially higher bottoming pressure allows an energy saving and an optimisation of the flows of heat, using gaseous methanol distilled in the bottoming stage to supply heat to the preliminary topping stage.

Preferably, a process without recovery of heat from the final distillation stage has the following pressures: topping pressure and final bottoming pressure about 1.5 bar; high pressure stage about 18-20 bar; medium pressure stage about 8-10 bar.

Preferably, a process with recovery of heat also from the final distillation stage is carried out with the following pressures: topping pressure about 1.5 bar; high pressure stage about 30 bar; medium pressure stage about 20 bar; minimum pressure (bottoming) stage about 5 bar.

It should be noted that the precise calculation of the pressures can be determined from the thermal balance of the evaporators/condensers considering the respective minimum Dt of heat exchange, temperature of the evaporating solution, etc. Indeed, the pressure also determines the temperature of the hot stream of gaseous methanol and, consequently, the condensation temperature of the methanol.

According to the embodiment, the only heat input for the distillation process can be represented by the heat of the maximum pressure stage and, possibly, by the heat of the topping stage. In general, the topping stage requires low temperature heat (low thermal level) and therefore it is advantageous to use the gaseous distilled methanol at high/medium pressure to heat an intermediate pressure stage or the bottoming stage. Preferably, the topping stage is heated with the heat recovered in the embodiments that provide a bottoming distillation at higher pressure, as described above.

The described topping and distillation stages in cascade are preferably implemented with respective refining columns. For each stage it is possible to use a single column or a plurality of columns in parallel, if necessary. Each column is connected to at least one bottom reboiler and possibly also to a top condenser. Some distillation columns can be connected to a reboiler/condenser represented by a single heat exchanger that performs the function of a bottom reboiler for a distillation column and of a top condenser for a column farther upstream in the cascade, operating at higher pressure.

The object of the invention is also a plant for carrying out the process, according to the attached claims.

Some advantages of the invention are as follows.

The invention makes it possible to save a substantial amount of energy, which can be about 0.20 Gcal per ton of methanol compared to the state of the art, i.e. about 30%. For a plant producing 5000 t/d of methanol, the energy saving comes to about 40 Gcal/h, equivalent to 3% of the total energy consumption of the plant including the distillation. Such an energy saving makes it possible to reduce the production cost of methanol. The consumption of cooling water for the condensers is also lower with respect to the state of the art.

The new process is also advantageous in terms of the capital cost, particularly for large-sized plants, more than 5'000 t/d. Since the production of distilled methanol is split into at least three refining columns, each of said three columns has a smaller diameter than distillation columns of known plant lay outs with one or two pressure levels. The weight and cost of the columns are also lower with respect to the prior art, due to the smaller volume and surface of the distillation plates, for the same production of distillate.

Another advantage is the possible replacement of air-cooled top condensers with more compact heat exchangers. Air-cooled top condensers are commonly used in methanol plants installed at locations with low availability of cooling water. Air-cooled top condensers are bulky and, although they do not consume water, consume electric energy. Their replacement with heat exchangers, advantageously having a tube bundle, which integrate the function of condensers and reboilers, is therefore advantageous.

DETAILED DESCRIPTION OF PREFERRED EMBODIMENTS OF THE INVENTION

Figure 1:
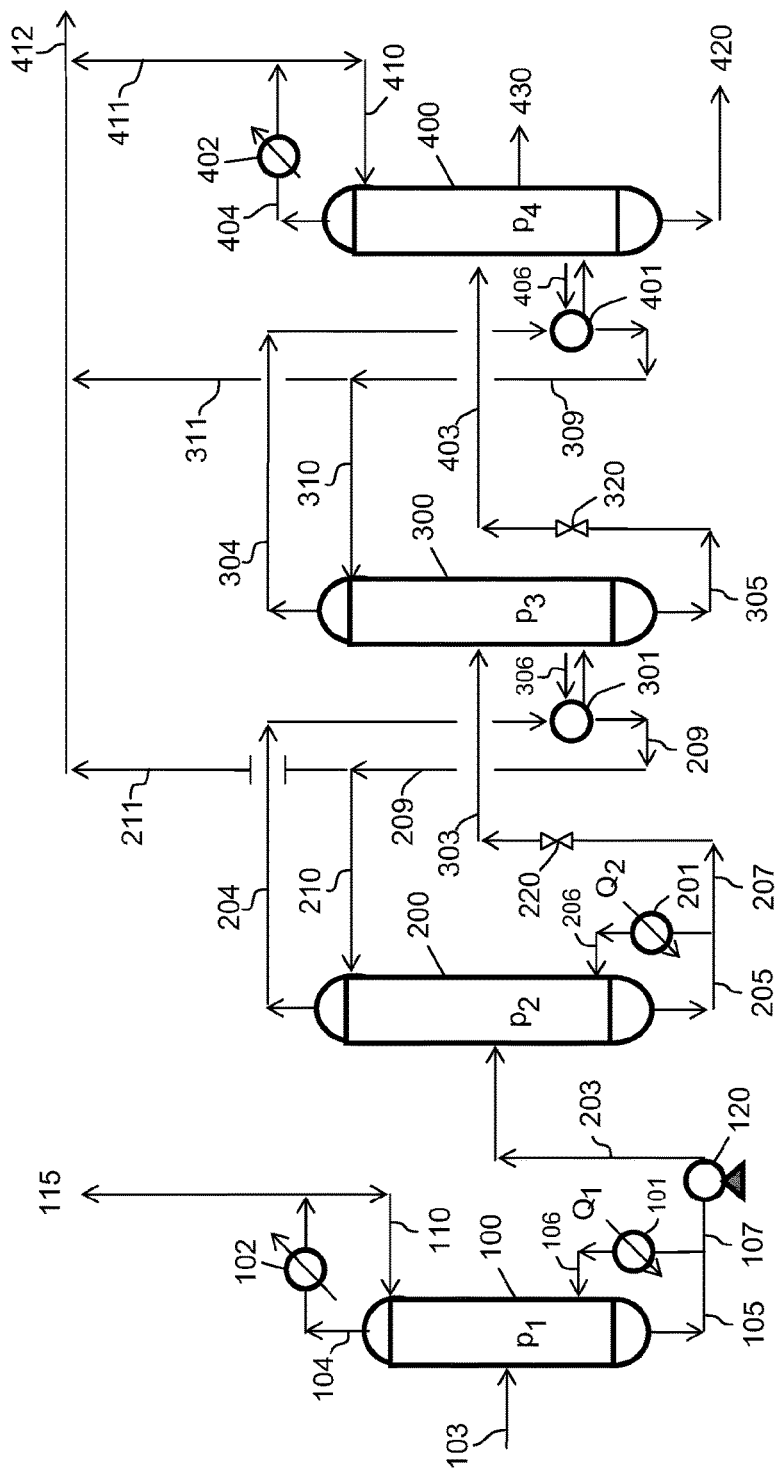
FIG. 1 is a diagram of a methanol distillation section according to an embodiment of the invention.
Figure 2:
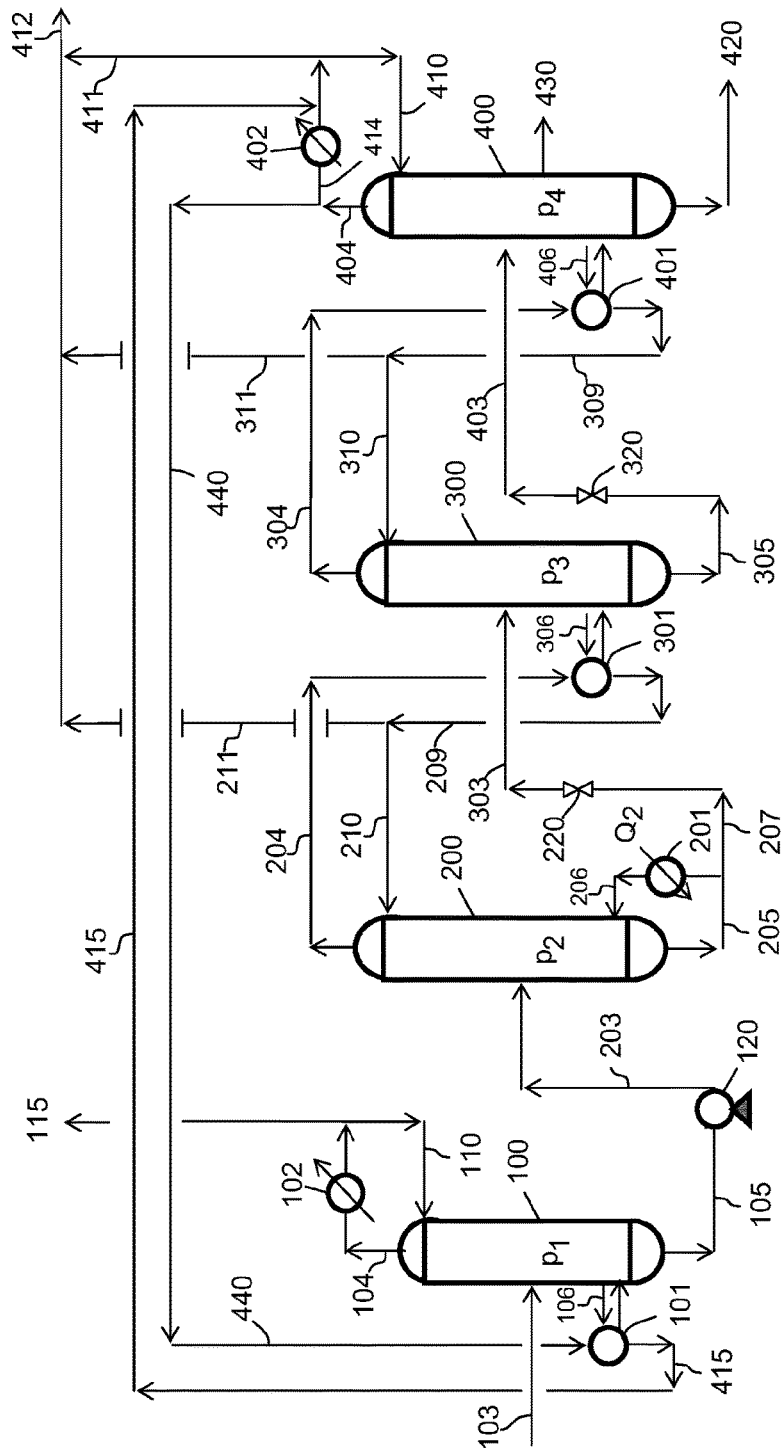
FIG. 2 is a diagram of a methanol distillation section according to another embodiment of the invention, in which the reboiler of the topping column is heated recovering heat from distilled methanol obtained in the bottoming column.

FIGS. 1-2 show example schemes of processes and plants according to some embodiments of the invention.

In essential terms, a stream 103 of crude methanol is subjected to topping refinement in a column 100, separating volatile components 104 and a first solution 105. Said solution 105 is then distilled to obtain methanol 412 with a required purity grade (for example AA).

The distillation of methanol in the examples of FIGS. 1-2 comprises three pressure levels, in a high pressure column 200, in a medium pressure column 300 and a low pressure (also known as bottoming) column 400, respectively.

The intermediate distillation stages, in columns 200 and 300, produce respective gaseous streams 204, 304 of distilled methanol, of the grade required by the process (e.g. AA). Said streams 204, 304 are used in the process to heat the column 300 and the column 400, respectively. FIG. 2 shows an embodiment where a stream of distilled methanol coming from the bottoming column 400 can be used to heat the topping column 100.

Consequently, the only heat inputs from the outside are represented by the heat Q1 and Q2 in the embodiment of FIG. 1, and by the heat Q2 in the embodiment of FIG. 2. It should be noted that the heat Q2 cannot be recovered inside the process since it is at maximum temperature.

The two embodiments are now described in greater detail.

FIRST EMBODIMENT

FIG. 1 shows a scheme that comprises a topping column 100, a bottoming column 400 and two distillation columns 200, 300. The distillation columns 200, 300 and 400 operate in cascade at decreasing pressures p2>p3>p4. The topping column 100 operates at a pressure p1 that is usually about 1.5 bar; the pressure p4 of the column 400, in this example, is substantially equal to the topping pressure p1, i.e. p4=~p1.

In the present description the concentrated and distributed pressure drops due to pipes, valves, auxiliary parts, etc. are not considered. Each column has a nominal pressure; the pressure of the top gas and pressure of the liquid extracted at the bottom are slightly different, as known to a man skilled in the art.

The topping column 100 comprises a bottom reboiler 101 and a top condenser 102. The columns 200, 300 and 400 comprise respective bottom reboilers 201, 301 and 401. The column 400 also has a top condenser 402.

The topping column 100 receives a flow of crude methanol 103 and separates a gaseous top stream 104 formed from volatile components lighter than methanol (light ends) and a bottom solution 105, containing methanol. A part 106 of said solution 105 is heated, preferably with at least partial evaporation, and recirculated through the bottom reboiler 101. The remaining part 107 of said solution 105 is fed to a pump 120 that feeds the high pressure column 200 with a stream of methanol solution 203. The stream 203 is substantially at the pressure p2, apart from the pressure drop in the supply duct to the column 200.

A part of the top stream 104 is condensed and recirculated as indicated by the line 110. The remaining part 115 is discharged or removed.

The column 200 separates a top stream 204 of gaseous methanol distilled at the pressure p2, and a bottom solution 205. Part of the bottom solution 205 is recirculated (line 206) to the bottom of the column 200 through the reboiler 201 and the remaining part (line 207) is fed to the subsequent second column 300. The stream 207 passes through a throttling valve 220 or equivalent, obtaining a stream 303 substantially at the pressure p3 that feeds the column 300 or rather the subsequent distillation stage.

The reboiler 101 of the topping column and the reboiler 201 of the high pressure column 200 are fed by external heat sources respectively indicated with the symbols Q1 and Q2. Said heat sources can be represented by steam condensing at a suitable pressure, if available, or other. In some embodiments the heat source can be a process gas.

The methanol solution 303 is further distilled in a stream of gaseous methanol 304 and a bottom solution 305. A flow of liquid solution 306 taken from the bottom of the column 300 is heated in the respective reboiler 301, to heat the bottom of the column 300 and maintain the distillation process. The flow 306, in equivalent embodiments, can also be a part of the flow 305.

Said reboiler 301 is heated by at least partial condensation of the stream of gaseous methanol 204, at high temperature and high pressure, coming from the top of the column 200. The stream 204 is at least partially condensed in the hot side of the reboiler 301 obtaining a flow of condensed methanol 209; a part of said condensate 209 is recirculated in the column 200 (line 210) and the remaining part (line 211) represents distilled methanol that is exported by the process.

In a substantially analogous manner, the stream of gaseous methanol 304 heats the column 400, heating a solution 406 in the reboiler 401. More specifically, the solution 305 expands at pressure p4 in the valve (or equivalent) 320, forming the methanol solution 403 that feeds the column 400. The stream 304 for example condenses in the reboiler 401 forming a liquid stream 309, which in part is recirculated in the column 300 (line 310) and in part represents distilled methanol 311.

The solutions 206, 306 and 406 preferably are evaporated, at least partially, in the reboilers.

The bottoming column 400 separates a further stream of gaseous methanol 404; a part 411 of said stream represents distilled methanol exported by the process, the remaining part 410 being reintroduced into the column 400. The overall flow of distilled methanol 412 comes from the streams 211, 311 and 411. The streams 211 and 311, at higher pressure, can be expanded in throttling valves or equivalent (not shown). The column 400 also produces a flow substantially of water 420 and a side stream 430 of fusel oil comprising roughly one percent residual methanol.

As can be seen in FIG. 1, the only external heat inputs, with respect to the distillation process, are represented by the sources Q1 and Q2. All of the heat of the columns 300 and 400, indeed, is recovered internally by the condensation of the gaseous streams of distilled methanol 204, 304.

It should also be noted that the reboiler 301 also operates as a top condenser of the column 200 since it condenses at least a part of the distilled methanol 204, forming the top recirculation stream 210. Hence it is also named reboiler/condenser. Similarly, the reboiler 401 operates as a top condenser of the column 300. Preferably, said reboiler/condenser 301, 401 is represented by a tube bundle exchanger, for example with evaporation of the solution 306, 406 in the shell side and condensation of the distillate 204, 304 in the tube side (or vice-versa). In other embodiments it is possible to use a plate exchanger with heat exchange plates housed inside a shell.

It is understood that the dual function of reboiler and condenser of the heat exchangers 301, 401 is a substantial advantage because it eliminates the top condensers of the prior art, for example using water or air, and relative consumption of water and/or electric energy for the fans.

Advantageously, the pressures p2 and p3 are determined as a function of the heat and the temperature level required by the reboilers 301 and 401, respectively. The distillation pressure, indeed, determines the temperature and reboilers need a temperature jump ($\Delta T$), typically of about 10° C. Thus, for example, the pressure p2 is determined so that the gaseous stream 204 has a temperature of a few degrees higher than the boiling temperature of the solution 306.

In some embodiments there can be a further heat recovery (not shown) from at least one of the streams 211, 311, 411. For example, the stream 211 has a relatively high temperature (over 100° C.) and in some embodiments it can be used to preheat the solution 203, so as to decrease the heat supply Q2; this is a significant advantage because the heat Q2 is the most expensive in terms of energy.

SECOND EMBODIMENT

FIG. 2 shows another preferred embodiment. The components that are equivalent to those of FIG. 1 are indicated with the same numerals.

Said FIG. 2 refers to an embodiment where the pressure p4 in the column 400 is substantially greater than the topping pressure p1. For example, the pressure p1 is about 1-1.5 bar and the pressure p4 is at least 2 bar, preferably 3-5 bar. In this case, the gaseous stream 404 of distilled methanol, taken from the top of the bottoming column 400, has a relatively high temperature and pressure (typically 3-5 bar and over 100° C.) and it can represent a useful heat source for the reboiler 101 of the topping column.

In the example of FIG. 2, a part 440 of said stream 404 is directed to the reboiler 101 and cooled, preferably condensed, in said reboiler 101, while a remaining part 414 is directed to the top condenser 402. The condensate 415, formed in the reboiler 101, joins the condensate coming out from the condenser 402, forming a flow of distilled methanol partly reintroduced in the bottoming column (flow 410) and partly exported (flow 411).

EXAMPLES

Example 1

A stream of crude methanol has the following composition: methanol CH3OH 83%, H2O 15%, dissolved gases 1.9%, impurities 0.1%. A production of 5000 t/d of methanol grade AA is assumed.

A conventional set-up, according to the prior art, comprises a topping column at a pressure of 1.5 bar, a bottoming column at a pressure of 1.5 bar, and a distillation column at a pressure of 8 bar and a temperature of about 130° C. In these conditions the following can be calculated: overall energy consumption for the bottom reboilers: 0.63 Gcal/ton (meaning per ton of distilled methanol); heat exchanged by the top condensers of the topping column and of the bottoming column: 0.60 Gcal/ton.

Now with reference to the diagram of FIG. 1, one has the following pressures and temperatures.

Pressure p1 in the topping column: 1.5 bar.
Temperature at the bottom of the column (flow 105): 90° C.
Flow 204: 19 bar, 163° C.
Flow 205: 171° C.
Flow 304: 9 bar, 132° C.
Flow 305: 144° C.
Pressure in the bottoming column: 1.5 bar.
Flow 404: 70° C.
In these conditions the following table has been calculated.

| Heat Q1 (reboiler 101) | Gcal/h | 37 |
| Heat Q2 (reboiler 201) | Gcal/h | 69 |
| Specific heat consumption | Gcal/ton | 0.50 |
| Heat exchanged in the top condenser 102 | Gcal/h | 28 |
| Heat exchanged in the top condenser 402 | Gcal/h | 70 |
| Specific heat exchanged in the condensers | Gcal/ton | 0.46 |

The invention in this example allows an energy saving of about 0.10 Gcal (20%) per ton of methanol with respect to the state of the art considered above. For a plant producing 5000 t/d of methanol, the energy saving comes to 21 Gcal/h, equivalent to 1.5% of the total energy consumption of the plant (including distillation). The set-up requires a heat source at a higher thermal level with respect to the state of the art, for example steam at about 11 bar or equivalent, but the reduction in energy consumption compensates for this requirement.

The consumption of cooling water for the condensers is also less with respect to the state of the art. In a typical situation the consumption of cooling water is equal to 46 m3 per ton of methanol, with a saving of 14 m3 per ton of methanol compared to the state of the art (−22%).

Example 2

Now referring to FIG. 2, the same conditions of the previous example apply, except:
pressure p4: 3.5 bar.
Temperature of the flow 404: 100° C.
Flow 204: 29 bar, 183° C.
Flow 304: 17 bar, 158° C.

It can be seen that the distilled vapour 404 coming out from the bottoming column 400 is now at a sufficient thermal level to heat the exchanger 101 and supply the heat Q1 that in FIG. 1 was coming from the outside. In these conditions the following can be calculated:

| Heat Q2 (reboiler 201) | Gcal/h | 84 |
|---|---|---|
| Specific heat consumption | Gcal/ton | 0.40 |
| Specific heat exchanged in the condensers 102 and 402 | Gcal/ton | 0.34 |

As can be seen, this embodiment allows a further energy saving.

The examples show that the advantages of the invention can be quantified as follows: saving of 35-40% of the energy for the reboilers of the columns with respect to the prior art; saving of 40-45% of cooling water for the top condensers of the columns with respect to the prior art (if water-cooled); reduction of about 40-45% in energy consumption for the distillation (both by cooling with air coolers, and by cooling with circulating water); reduction of the maximum diameter of the refining columns, and therefore greater single-train capacity for the same maximum column diameter allowed; reduction of the investment cost required for the utilities system: cooling water and electric system; saving of the cost of the internals of the columns.

The invention claimed is:

1. A process for refining crude methanol, comprising:
at least three distillation stages operating in cascade at respective decreasing pressures, comprising at least a first distillation stage at a maximum distillation pressure, a second distillation stage at a medium distillation pressure, and a final distillation stage at a minimum distillation pressure,
comprising a stage of preliminary treatment named a topping stage, operating at a topping pressure in which said stream of crude methanol is separated into at least one gaseous stream of volatile components, and a liquid solution fed to said first distillation stage;
wherein said first and second distillation stage each produce at least one first gaseous stream and at least one second gaseous stream of distilled methanol, respectively, and a respective solution containing methanol that is fed to the next distillation stage, and said final stage produces at least one gaseous stream of distilled methanol and a solution made up essentially of water;
wherein said at least one first gaseous stream of distilled methanol, produced in the first distillation stage, and said at least one second gaseous stream of distilled methanol, produced in the second distillation stage, are used as heat sources to heat up at least said second distillation stage and said final distillation stage, respectively, and
wherein said maximum distillation pressure being comprised between 10 and 35 bar.

2. The process according to claim 1, wherein said at least one first and said at least one second gaseous stream of distilled methanol supply all of the heat, respectively, for said second distillation stage and said final distillation stage.

3. The process according to claim 1, wherein said at least one first and said at least one second gaseous stream of distilled methanol supply heat to said distillation stages by indirect heat exchange with a respective stream of a solution containing methanol to be distilled.

4. The process according to claim 3, wherein said gaseous streams of distilled methanol are at least partially condensed during said heat exchange, obtaining respective streams of distilled methanol in liquid state.

5. The process according to claim 4, wherein a part of said streams of distilled liquid methanol is returned to the respective distillation stage, and a remaining part represents distilled methanol coming out from the process.

6. The process according to claim 1, wherein said minimum distillation pressure is substantially greater than said topping pressure, and a gaseous stream of distilled methanol produced in the last distillation stage, operating at said minimum pressure, is used to at least partially heat said preliminary topping treatment stage.

7. The process according to claim 6, wherein said gaseous stream of distilled methanol produced in the last distillation stage is at least partially condensed through indirect heat exchange with a solution containing methanol at the topping pressure.

8. The process according to claim 6, wherein the topping pressure is roughly equal to atmospheric pressure, and the minimum distillation pressure is at least 2 bar.

9. The process according to claim 1, comprising said three distillation stages at said high pressure, said medium pressure and said minimum pressure, respectively, and comprising a preliminary topping stage, wherein the topping pressure is about 1.5 bar, and
the minimum distillation pressure is roughly equal to a topping pressure, said high pressure is about 20 bar and said medium pressure is about 8-10 bar,
or
the minimum distillation pressure is at least 3 bar and preferably about 5 bar, said high pressure being about 30 bar and said medium pressure being about 15-20 bar.

10. The process according to claim 9, wherein the distillation stages and the preliminary topping stage are each carried out in at least one respective refining column.

11. The process according to claim 1, wherein said maximum distillation pressure is at least 20 bar.

12. The process according to claim 3, wherein the solution is at least partially evaporated by means of the effect of said heat exchange.

13. The process according to claim 7, wherein said solution is at least partially evaporated through the effect of said heat exchange.

14. The process according to claim 8, wherein the minimum distillation pressure is about 5 bar.

\* \* \* \* \*